(12) United States Patent
Heine

(10) Patent No.: US 9,861,454 B2
(45) Date of Patent: Jan. 9, 2018

(54) APPARATUS FOR TEMPOROMANDIBULAR JOINT-RELATED CORRECTIONS OF TOOTH POSITION

(71) Applicant: Gernot Heine, Wedemark-Mellendorf (DE)

(72) Inventor: Gernot Heine, Wedemark-Mellendorf (DE)

( * ) Notice: Subject to any disclaimer, the term of this patent is extended or adjusted under 35 U.S.C. 154(b) by 268 days.

(21) Appl. No.: 14/385,884

(22) PCT Filed: Mar. 19, 2013

(86) PCT No.: PCT/EP2013/000829
§ 371 (c)(1),
(2) Date: Sep. 17, 2014

(87) PCT Pub. No.: WO2013/139467
PCT Pub. Date: Sep. 26, 2013

(65) Prior Publication Data
US 2015/0079531 A1    Mar. 19, 2015

(30) Foreign Application Priority Data
Mar. 19, 2012 (DE) .................. 10 2012 005 323

(51) Int. Cl.
*A61C 3/00* (2006.01)
*A61C 7/36* (2006.01)
*A61C 7/08* (2006.01)

(52) U.S. Cl.
CPC . *A61C 7/36* (2013.01); *A61C 7/08* (2013.01)

(58) Field of Classification Search
CPC ........................ A61C 7/08; A61C 7/12–7/36
(Continued)

(56) References Cited

U.S. PATENT DOCUMENTS 5,975,893 A * 11/1999 Chishti .................. A61C 7/00
433/24
6,210,162 B1   4/2001 Chishti
(Continued)

FOREIGN PATENT DOCUMENTS

CN    1260698 A    7/2000
CN    101636122 A   1/2010
(Continued)

OTHER PUBLICATIONS

Chinese Search Report.
English Translation of Previously Filed Interational Preliminary Report for Application No. PCT/EP2013/000829.

*Primary Examiner* — Stephen R Crow
*Assistant Examiner* — Garrett Atkinson
(74) *Attorney, Agent, or Firm* — Gerald E. Hespos; Michael J. Porco; Matthew T. Hespos

(57) ABSTRACT

The invention relates to an apparatus for temporomandibular joint-related corrections of tooth position, taking into account a variant of the registration or construction of the bite predetermined by the user.
The invention is characterized in that a base module extending at least on the occlusion-bearing part of one side of the jaw is supported in an intermaxillary manner and has cavities formed by a setup technique to accommodate teeth, by means of which the tension forces necessary for tooth movements can act on the teeth, in that the base module has a three-dimensionally defined jaw support designed in accordance with specifications of the user, and in that the jaw support is formed by bite blocks and/or interceptors which have cavities filled with a filling material of predeterminable elasticity.

20 Claims, 12 Drawing Sheets

(58) Field of Classification Search
USPC .......................................... 433/8–12, 18–24
See application file for complete search history.

(56) References Cited

U.S. PATENT DOCUMENTS

| | | | |
|---|---|---|---|
| 6,217,325 B1 | 4/2001 | Chishti | |
| 6,398,548 B1 | 6/2002 | Muhammad | |
| 6,524,101 B1 | 2/2003 | Phan | |
| 6,572,372 B1* | 6/2003 | Phan | A61C 7/00 433/18 |
| 6,626,666 B2 | 9/2003 | Chishti | |
| 6,629,840 B2 | 10/2003 | Chishti | |
| 6,699,037 B2 | 3/2004 | Chishti | |
| 7,134,874 B2 | 11/2006 | Chishti | |
| 7,220,122 B2* | 5/2007 | Chishti | A61C 7/00 433/24 |
| 7,474,307 B2 | 1/2009 | Chishti | |
| 7,874,836 B2* | 1/2011 | McSurdy, Jr. | A61C 7/10 433/6 |
| 8,105,080 B2 | 1/2012 | Chishti | |
| 8,454,358 B2* | 6/2013 | Wahab | A61C 7/08 433/215 |
| 8,562,337 B2* | 10/2013 | Kuo | A61C 7/08 433/6 |
| 8,562,340 B2 | 10/2013 | Chishti | |
| 8,708,697 B2* | 4/2014 | Li | A61C 7/08 433/18 |
| 8,864,493 B2* | 10/2014 | Leslie-Martin | A61C 7/08 433/6 |
| 9,022,781 B2* | 5/2015 | Kuo | A61C 7/002 433/24 |
| 9,119,691 B2* | 9/2015 | Namiranian | A61C 7/08 |
| 9,161,824 B2* | 10/2015 | Chishti | A61C 7/00 |
| 2001/0002310 A1 | 5/2001 | Chishti | |
| 2001/0006770 A1 | 7/2001 | Chishti | |
| 2001/0008751 A1 | 7/2001 | Chishti | |
| 2001/0009753 A1 | 7/2001 | Chishti | |
| 2003/0207224 A1 | 11/2003 | Lotte | |
| 2004/0009449 A1* | 1/2004 | Mah | A61C 7/10 433/7 |
| 2004/0110110 A1 | 6/2004 | Chishti | |
| 2004/0134499 A1* | 7/2004 | Sabbagh | A61C 7/00 128/859 |
| 2004/0166456 A1 | 8/2004 | Chishti | |
| 2006/0286501 A1 | 12/2006 | Chishti | |
| 2009/0253100 A1* | 10/2009 | McCance | A61C 7/08 433/196 |
| 2011/0005527 A1* | 1/2011 | Andrew | A61C 7/08 128/848 |
| 2012/0244488 A1 | 9/2012 | Chishti | |

FOREIGN PATENT DOCUMENTS

| | | |
|---|---|---|
| CN | 201968851 U | 9/2011 |
| DE | 102004007008 A1 | 9/2005 |
| DE | 10 2008 157226 | 3/2010 |
| DE | 10 2009 009 916 | 9/2010 |
| DE | 10 2010 012 702 | 10/2010 |
| JP | H11155884 A | 6/1999 |
| JP | 2004525261 | 5/2004 |
| WO | 2010087824 | 8/2010 |

\* cited by examiner

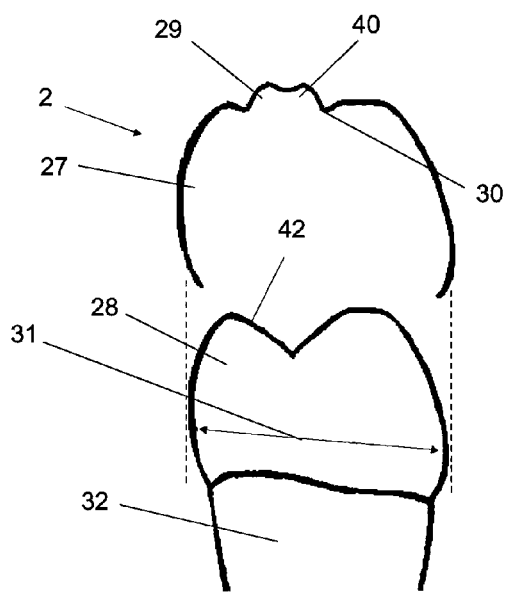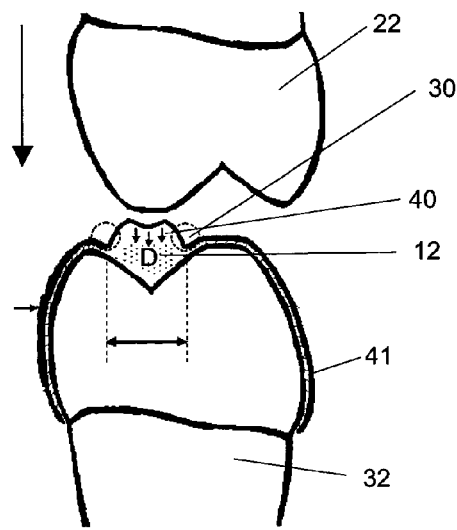
Fig. 12                                Fig. 13

APPARATUS FOR TEMPOROMANDIBULAR JOINT-RELATED CORRECTIONS OF TOOTH POSITION

BACKGROUND

1. Field of the Invention

The invention relates to an apparatus for temporomandibular joint-related corrections of tooth position, taking into account a variant of the registration or construction of the bite predetermined by the user.

2. Description of the Related Art

Temporomandibular joint-related corrections of tooth position have hitherto been performed using apparatuses for orthodontic treatment which are distinguished by their biomechanical characteristics. Different orthodontic treatment tasks are performed successively on patients. The treating professional or user must wait until a patient has reached the correct dentition age or the necessary level of functional-therapeutic progress in order for the next apparatus-based treatment technique to be applied.

In dentistry, functional therapy is understood to mean those measures intended to correct disorders of the neuromuscular and articular control of the masticatory system. To accomplish such corrections, suitable apparatuses are applied in the patient's oral cavity.

When biting, the position of the temporomandibular joints is defined exclusively by the contact between the teeth of the maxilla and mandible (occlusion contact). The possible movements of the mandible and of the temporomandibular joints are also determined by the geometry of the tooth surfaces when tooth contact occurs. Thus, if an impairment of the functioning of the musculature and joints resulting from missing or incorrectly positioned teeth requires treatment, apparatuses designed to therapeutically modify the occlusion process are used. Such apparatuses are usually made from spray-on plastic or a combination of a Miniplast splint with a plastic functional surface applied to it.

In functional orthodontic apparatuses, too, the position of the mandible with respect to the maxilla is altered. In general, such apparatuses are used in younger patients who are still growing and are in the mixed dentition stage. In addition to "bite blocks", such "braces" have construction elements which generally act on the surrounding tissue structures by exerting displacement functions. Their influence on regulating tooth position is thus generally passive, and is expanded in most embodiments simply by means of wire spring elements and screws.

All prior art orthodontic apparatuses are designed only for limited portions of the orthodontic treatment spectrum, and can generally only be used for patients in particular age groups or with specific forms of dysgnathia (malformation of the masticatory organ).

A method and a device for incrementally moving teeth are known from DE 698 18 045 T2. Such aligner apparatuses (series of transparent foils for the gradual correction of tooth position) can implement orthodontic tooth movements on the basis of known setup methods.

The disadvantage of this is that only teeth and prosthetic teeth are enveloped. The thickness of the material used for the foils undesirably modifies the spatial relationship between maxilla and mandible which is aimed for in the case of the patient. This apparatus itself does not permit an almost freely selectable spatial support of the jaws in relation to each other.

A method for the computer-assisted manufacture of an orthodontic bite splint is known from DE 10 2009 009 916 A1, in which the bite splint has an upper masticatory surface with which the opposing jaw of a patient makes contact when the splint is in place.

The disadvantage of this is that, when installed, the known apparatus or bite splint only modifies the positional relationship between the maxilla and mandible. Such passive bite splints neither provide the treating professional with a diagnostic indication of pathological muscular hyperactivity nor do they permit the temporomandibular joint-related reconstruction of a healthy masticatory and joint system.

A passive bite spint is known from DE 10 2010 012 702 A1 in which a retention-forming part of the splint overlying the teeth is supplemented with a replaceable part oriented toward the opposing jaw. This part should have a "cranially concave calotte shape".

This known apparatus or bite splint also has the above-mentioned drawbacks, and merely alters the spatial relationship between maxilla and mandible.

The task of the present invention is thus to create an apparatus which combines the biomechanical characteristics of groups of orthodontic apparatuses previously employed separately into a new overall apparatus-based and therapeutic strategy.

SUMMARY OF THE INVENTION

The invention relates to an apparatus for temporomandibular joint-related corrections of tooth position, wherein a base module extending at least on the occlusion-bearing part of one side of the jaw is supported in an intermaxillary manner and has cavities to accommodate teeth, by means of which the tension forces necessary for tooth movements can act on the teeth. The base module has a three-dimensionally defined jaw support designed in accordance with specifications of the user, and the jaw support is formed by bite blocks and/or interceptors that have cavities filled with a filling material of predeterminable elasticity.

The invention permits the dimensionally accurate targeted support of the jaws relative to one another up to the point of occlusion contact (in accordance with the user's assigned values) as well as the replacement of occlusion-supporting elements while tooth movements are actively being carried out.

In addition to extensive three-dimensional corrections of tooth position, the apparatus in accordance with the invention enables the spatially controlled correction of a malpositioned temporomandibular joint by means of creating and providing the jaw support as a 4-D apparatus (four-dimensional apparatus), using as the fourth dimension the principle of spatial coupling between the rows of teeth and the temporomandibular joints already when planning the tooth movement and the design of the device with the aid of 4-D software. The information regarding the relative spatial positions of the teeth on the one hand and the temporomandibular joint heads in relation to their joint sockets on the other can be provided by known medical imaging methods. Both CT (computerized tomography) and DVT (dental volume tomography) imaging currently provide STL data sets which may be combined with 3-D planning software programs.

In accordance with one embodiment of the invention, at least one supplementary module and/or auxiliary parts are provided.

By virtue of their modular construction, the occlusion-supporting elements themselves can also be reversibly connected with mechanisms and auxiliary parts to actively transfer forces and torques. Corrections of tooth position can thus be carried out in stages, through successive changes of one or more device components or apparatus components, as well as through combining them with mechanisms and elastic elements which can be attached to these components (modules) and directly to teeth and prosthetic restorations (including implants).

Various different orthodontic treatment tasks, which would otherwise have to be performed in succession on a patient, can thus be carried out simultaneously and more efficiently. The treating professional or user need no longer wait until the patient has reached the correct dentition age or the necessary level of functional-therapeutic progress in the treatment process for a new apparatus technique to be applied. Nearly all known treatment tasks can be directly resolved through the exchange or recombination of individual modules if it appears indicated during the course of a therapy.

In addition, the spectrum of medical treatment is expanded by the possibility of simultaneously applying intermittent forces in combination with the controlled and variable support of the occlusion and thus of the temporomandibular joints. In particular, vertical corrections of the alveolar processes and corrections of the positions of the temporomandibular joints can for the the first time be performed simultaneously with extensive corrections of tooth positions. Principles of setup technologies (digital, analog, etc.) can now be combined with functional-therapeutic methods and simultaneously interact with apparatus modules attached to teeth, not simply by overlapping and enveloping them, but by engaging them directly for the transfer of forces and torques.

It should be emphasized that it is possible to integrate a design of the occlusion-bearing areas that is suitable for functional-therapeutic purposes into the apparatus itself. This is not known from previous orthodontic apparatuses in widespread use (multi-bracket apparatuses and aligner technologies).

The design of the apparatus fundamentally takes into account a variant of the registration or construction of the bite provided by the treating professional or user. The invention opens up this possibility for the first time with the three-dimensionally variable structure of its base module. Its underlying modular concept enables the combination of biomechanically advantageous characteristics of a wide range of known groups of devices, as well as preferably software-based planning and RP (rapid prototyping) production processes in a single apparatus.

For the first time, the occlusion-bearing components of an orthodontic apparatus concept also need not be bonded to teeth or prosthetics like fixed bite block devices or cranio-orthopedic positioning apparatuses (COPA). A sequence of devices can thus be created in which each individual therapeutic device corrects tooth positions in small stages, as in the case of aligner technologies, while constantly maintaining the planned spatial relationship between maxilla and mandible. It is therefore now also possible for the first time to modify the spatial relationship of the jaws without having to alter or remove bite block aids that are fixed in the mouth.

The base module in this system has a spatially defined jaw support in accordance with the specifications of the user. The jaw support is formed by bite blocks and/or interceptors which have cavities filled with a filling material of predeterminable elasticity.

A liquid or gaseous filling for the cavities does little to improve the masticatory pressure stability of the bite block areas that are created. As a result, a patient performing parafunctions (grinding or pressing) in a manner injurious to health will crush the bite block designs illustrated (assuming that standard foil thicknesses are used). This base module thus also constitutes a new functional-diagnostic instrument which can simultaneously perform targeted corrections of tooth position.

In the event that rubber-elastic filling materials are used as a supplementary module, which can be reversibly connected with the bite block cavities through mechanical friction or retention, continuous masticatory pressure load will result in the intrusion of the under the bite block cavity lying tooth underlying tooth.

Extremely hard filling materials cause a sensitive bite block reaction. When subjected to a sudden stress, they trigger the "cherry pit reflex", in which the jaws open spontaneously. Even if this stress situation continues, the body's sensory reaction ensures that a permanent masticatory pressure load and consequent intrusions are now avoided.

In a further embodiment of the invention, the base module has a functional module attached to it which can be reused when the base portion is modified.

In accordance with another embodiment of the invention, the base module can interact with the supplementary module, which can be arranged on the opposing jaw.

In accordance with a further embodiment of the invention, the base module or its functional module is connected to the supplementary module by an elastic connecting element.

The orthodontically effective and thus generally active base modules are therefore characterized by being removable from the mouth for the purpose of food intake and easier oral hygiene, as is the case with standard aligners. These base modules in particular also feature the spatially defined jaw support in accordance with the user's specifications (similar to functional-therapeutic bite splints) without needing additional fixed bite blocks in order to overcome even larger intermaxillary differences. These base modules are custom-designed for each patient and can be assembled with inexpensively produced, standardized functional modules (one simple example is miniature expansion screws, the geometry of which can be integrated as a data set into the 3-D planning of the base module). In this way, the whole apparatus need not be discarded after the completion of minor tooth movements (as is the case with aligners and elastic orthodontic devices such as positioners). Supplementary modules are auxiliary parts that function as anchors or abutments or have a retention function, and they are preferably bonded to tooth surfaces or prosthetics and thus interact with base and functional modules through direct contact or connecting elements. It may thus be possible to save on the number of apparatuses, which would make both economic and ecological sense.

According to a further embodiment of the invention, the inner side of the base module has a supplementary module in the form of an expansion arch affixed to the base module. This permits the base module to be constructed with minimal material consumption, and it can transmit additional expansion forces to the tooth surfaces via the expansion arch.

According to a further embodiment of the invention, the base module has receptacles for auxiliary parts on its inner side facing away from the outer.

According to a further embodiment of the invention, the receptacles form pockets for receiving the auxiliary parts, and these are formed as attachments arranged on the outer side of teeth, and they also have a grooved receiving element for elastics to connect the modules (e.g. elastic bands).

As a basic design attribute, the apparatus takes into account a variant of the registration or construction of the bite specified by the treating professional. This specification defines the dimensions of the occlusion-supporting component of the base module. The base modules run along the occlusion-bearing portion of one side of the jaw, and can be connected to the base module of the other side of the jaw. Depending on production, this can also be connected to a carrier foil overlaying the teeth (in this case a supplementary module variant) in order to distribute tension forces across the entire dental arch. In addition, the base module is based on a setup (it makes no difference whether it is analog, digital or comparable). Thus, in addition to supporting the temporomandibular joint, corrections of tooth positions are also made, thereby differentiating the base module from Miniplast splints, bite splints, and aligners. In order to enable purely passive tooth movements, as in the case of functional-orthodontic devices (e.g. Bionator), the intended tooth movements can be structured as cavities.

In order for the base modules described above to carry out additional functions beyond orthodontic tooth movements and the spatial support between maxilla and mandible, they may be connected to other modules.

Cheek guards and lip supports, as well as tensioning hooks intended to interact with modules affixed to the teeth, and representing further advantageous embodiments of supplementary modules, complement the therapeutic effectiveness of the basic apparatus through various mechanical connections with it.

If connected reversibly by plug or similar connectors, these supplementary modules need not be replaced together with the base module for every step of an orthodontic tooth movement. Rather, with the use of the connecting elements described below, they can be removed and reused multiple times.

In order to amplify the force and torque effects of the apparatus on the teeth and alveolar bones, auxiliary parts are required which can be affixed to teeth and dental prosthetics by means of various adhesive connections. As the biomechanical characteristics and potential applications are different from those of aligner and multi-bracket apparatuses, other advantageous embodiments of attachments are also required. An example of such an embodiment would be one which, through adhesion to tooth surfaces, can both increase the retention of the base module on the tooth surface as well as transfer defined forces directly to the tooth to be moved by means of elastics placed in the embedded guide. An apparatus in accordance with the invention can be produced by, in a first step, creating a spatially 3-dimensionally defined positional relationship between maxilla and mandible by changing the form of the tooth surface by means of wax-up in an articulator, and, in a second step, creating by means of a physical or optical impression an overimpression of the model geometry reconfigured with bite blocks and interceptors.

In a third step, a jaw relation of a patient previously transferred to the articulator can be transferred to a setup model created using an analog or digital process.

The apparatus can be adapted for the incremental movement of teeth and various corresponding modules can be produced.

The creation of reversible connections between the individual modules and auxiliary parts requires miniature versions of known push, plug, or other detachable locking mechanisms.

Because removable orthodontic apparatuses have thus far been produced almost exclusively by hand using spray-on acrylates, various thermoplastic deep drawn foils, or—in the case of positioners—silicone, the physical integration of the connecting elements is challenging.

Current 3-D design software enables the virtual connection of individual predefined data sets and their integration into an individually designed form of recording.

Multiple software vendors offer programs for the virtual correction of tooth positions which are capable of simulating auxiliary parts affixed to virtual tooth surfaces.

The additional development steps needed for the virtual planning of the apparatus described and the tooth movements associated with its use require the integration of complex geometries and mechanisms, the dimensions of which can be modified e.g. by screws. Accordingly, the simulation of the virtual tooth movements must also be capable of simulating the biomechanical characteristics of the apparatus and the associated relative movement of an apparatus with regard to the apparatus-bearing tooth surfaces.

In a simple design of a base module already capable of being produced, a spatially 3-dimensionally defined positional relationship between maxilla and mandible can initially be obtained through the modification of the form of the tooth surface using the wax-up technique in an articulator. Such a positional relationship is always based on a transfer of the position of the maxilla in relation to the skull and on a process-dependent configuration of a mandibular position registration.

The basis for a new model incorporating the shape of the bite blocks and interceptors is created in accordance with an overimpression taken of the model geometry as reconfigured with bite blocks and interceptors, using physical or optical impressions. In this way, the jaw relation of a patient previously transferred to the articulator can be transferred to a setup model. All production steps can be carried out as described herein using analog or digital methods.

A replaceable and functional supplementary module is realized by filling the cavity between the deep-drawn foil and the covered occlusion surface. If a deep-draw technique is used to produce the body of the base module, the correct dimensioning of the registration-related intermaxillary support should be reestablished by reduction of the thickness of the foil material in the occlusion-bearing area. This also opens up contact between the underlying supplementary module and the opposite dentition. The desired controlling effect on the vertical therapeutic effect is thus made even more direct. Through the exchange of the fillings and their vertical expansion, a progressive tooth intrusion can be realized using rubber-elastic inserts.

The elastic resistance under masticatory pressure loads can also be controlled by means of the geometry of the interceptors in the anterior region of the side teeth and by the expansion of the support surface in the area of the posterior intermaxillary support.

In order for the jaw relation to be kept constant while orthodontic corrections of tooth positions are carried out, a selective setup in particular of those teeth not directly stressed by the support is performed. The path of the desired tooth position correction can be determined for these teeth using the same principles. However, it is necessary to first expose the entire tooth circumference related to the corrective movement. The prosthetic tooth equator is thus not stressed for these areas, i.e. for the tooth movement. The necessary orthodontically effective forces are then generated preferably (because it is inexpensive and saves on devices) by means of auxiliary parts using inter- or intramaxillary elastics which are linked to the tooth to be corrected by means of the notch in the attachment.

Further details of the invention can be obtained from the following detailed description and from the attached drawings, in which examples of preferred embodiments of the invention are depicted.

BRIEF DESCRIPTION OF THE DRAWINGS

FIG. 12 is a lateral sectional view of a base module and a lateral detail view of the associated tooth with base module not yet installed.

FIG. 13 is a lateral sectional view of the base module of FIG. 12 installed on the associated tooth and a tooth outlined on the jaw opposite.

DETAILED DESCRIPTION

Figure 1:
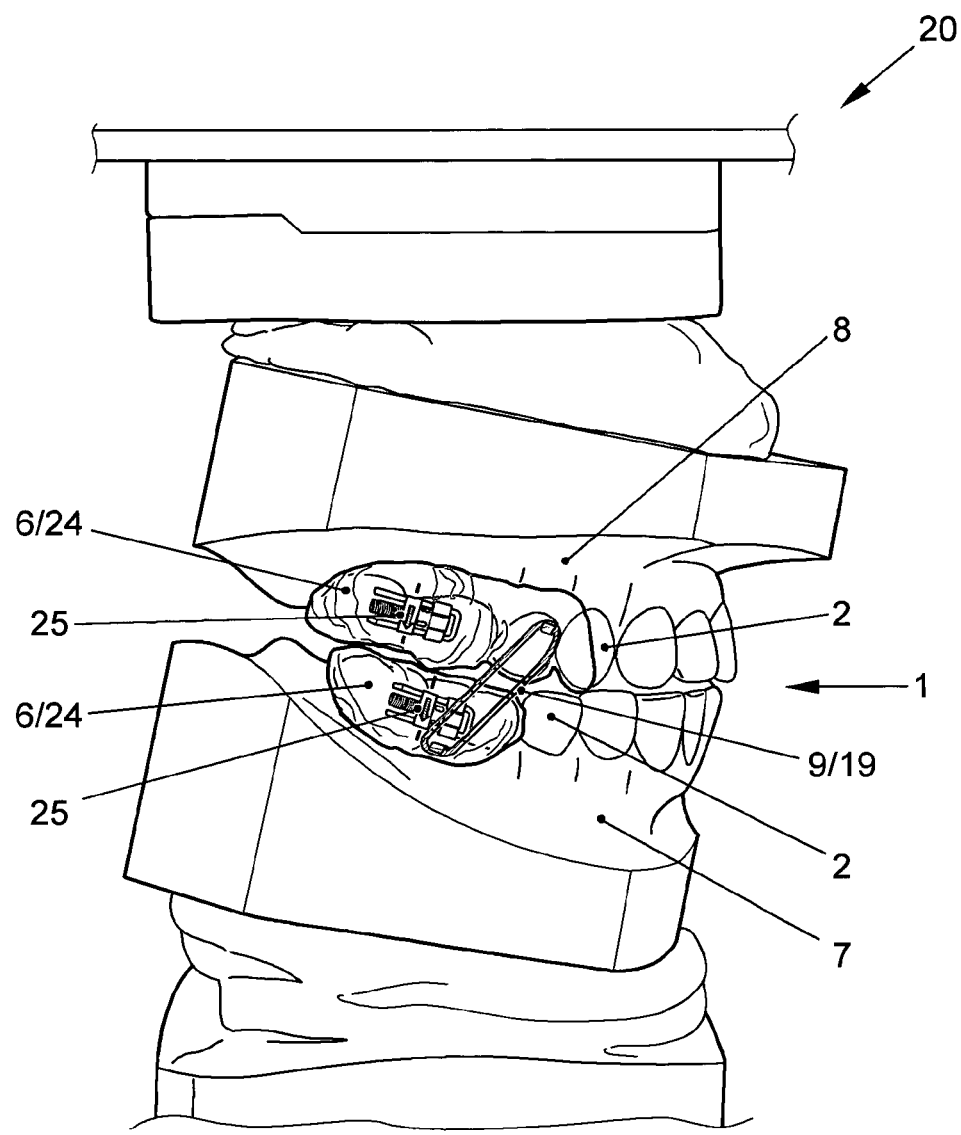
FIG. 1 side elevational view of an apparatus arranged in an articulator.

An apparatus 1 comprises essentially a base module 2, a supplementary module 3, and auxiliary parts 4.

The base module 2 has a spatially defined jaw support 5. A functional module 6 attached to the base module 2 can be reused when the base part or base module 2 is modified.

The base module 2 can interact with the supplementary module 3 which is capable of being arranged on the respective opposing jaw 7, 8.

Figure 4:
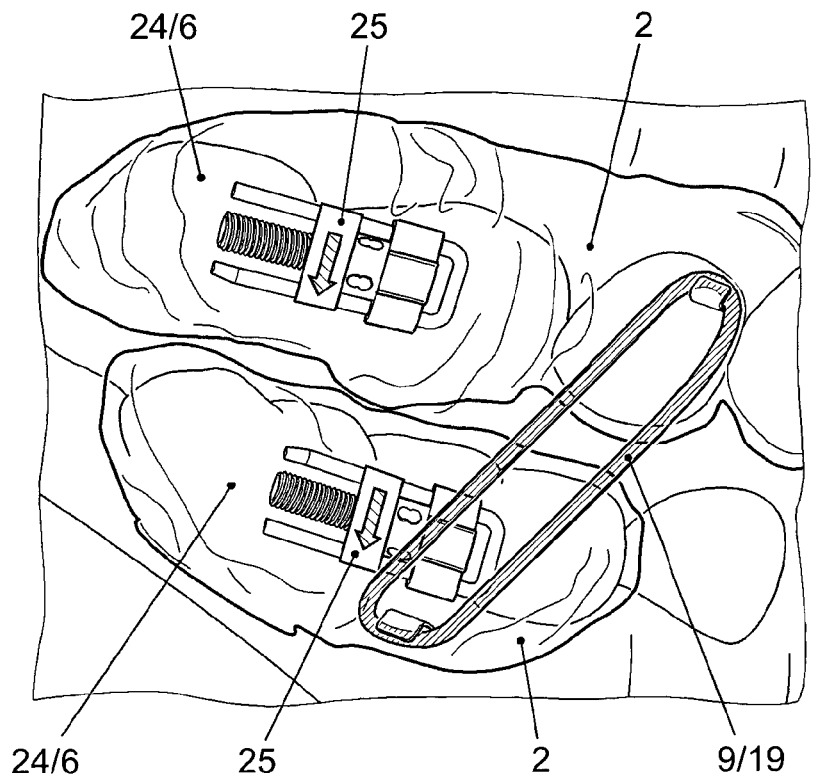
FIG. 4 is a lateral detail view on an enlarged scale of the supplementary modules of FIG. 1.
Figure 5:
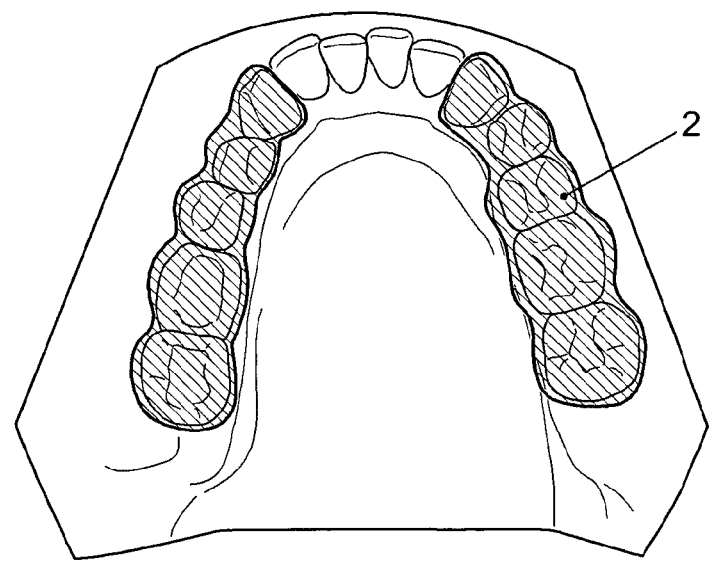
FIG. 5 is a top view of a base module.
Figure 6:
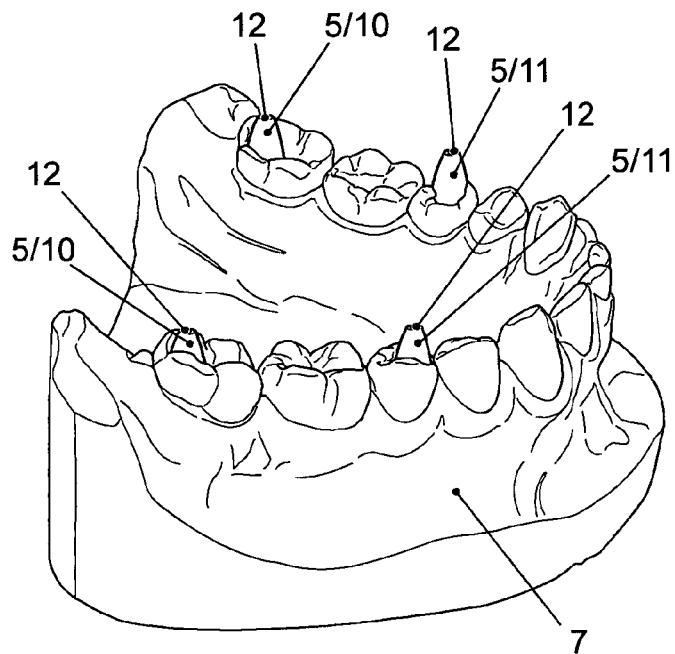
FIG. 6 is a spatial depiction of a mandibular impression with functional bite block and interceptor.
Figure 7:
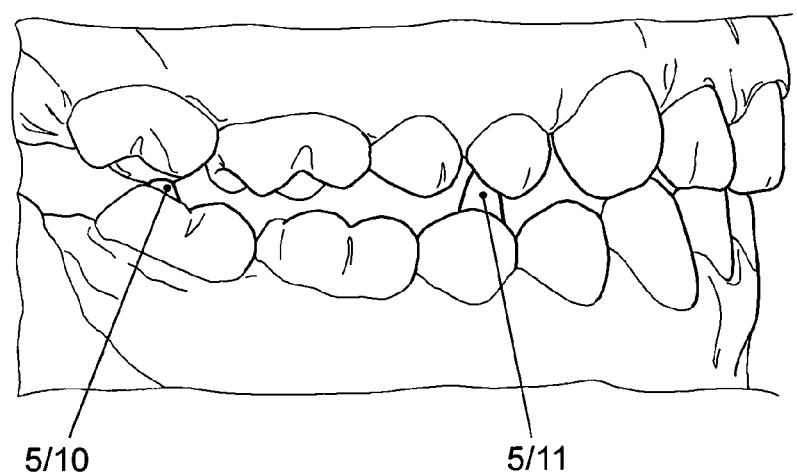
FIG. 7 is a lateral view on an enlarged scale of the occlusion-bearing supports mounted in the articulator.

In accordance with the exemplary embodiment of FIGS. 1 and 4, the base module 2 or its functional module 6 is connected to the supplementary module 3 via an elastic connecting element 9 (elastic).

Figure 8:
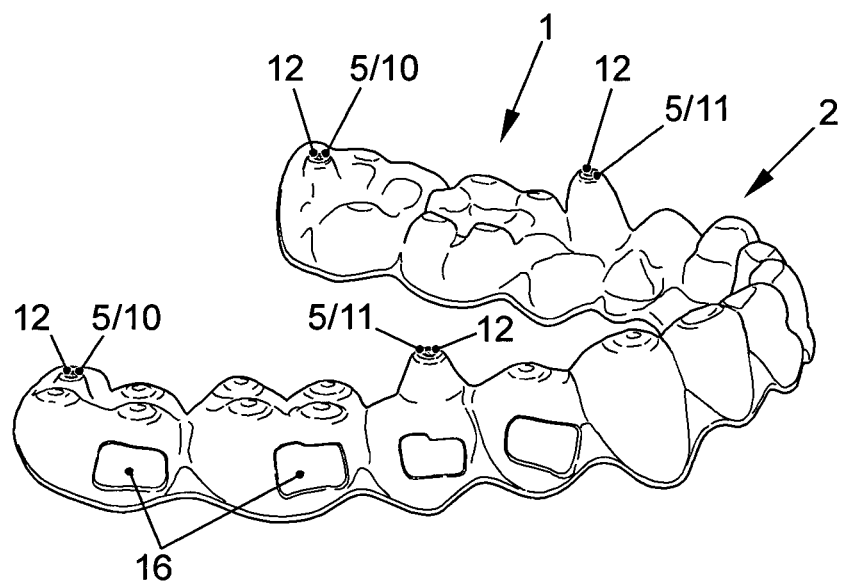
FIG. 8 is a perspective view of a simple base module with integrated temporomandibular joint-related support.
Figure 9:
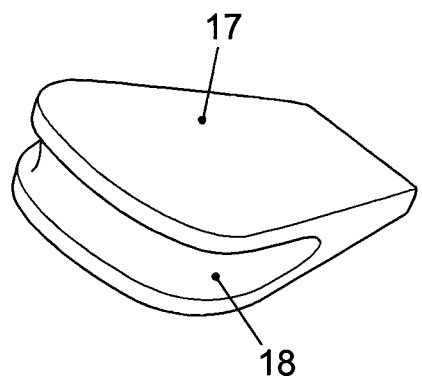
FIG. 9 is a perspective view, on an enlarged scale, of an auxiliary part formed as an attachment.
Figure 10:
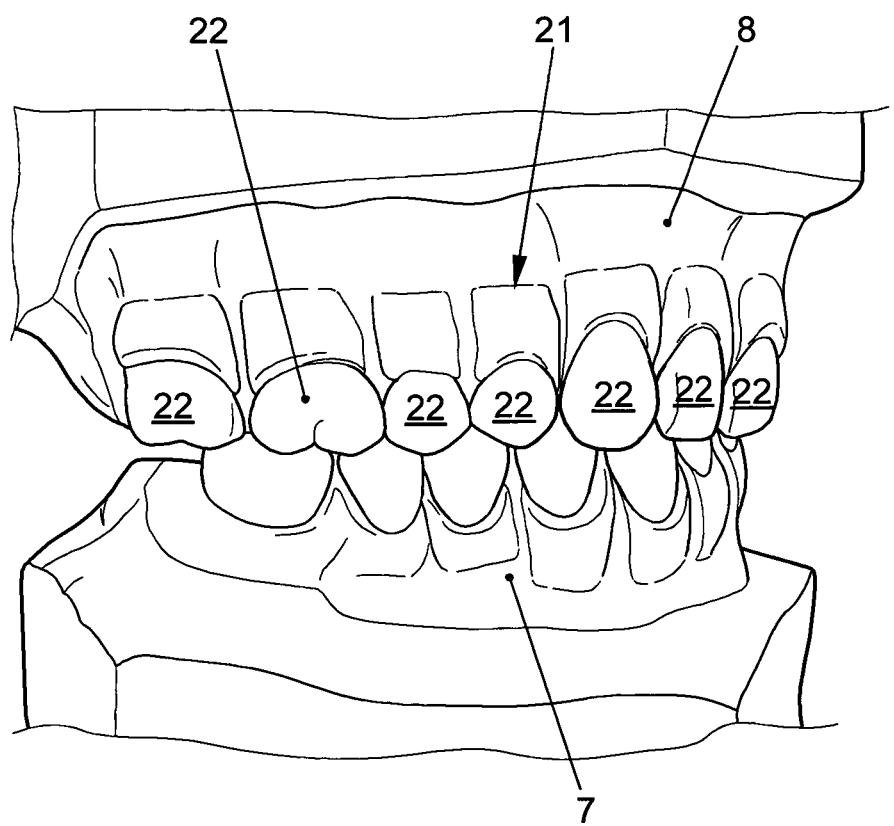
FIG. 10 is a perspective view of a known setup model in which the tooth models in the maxilla are each capable of being moved to an intended position.

In accordance with the exemplary embodiment of FIG. 8, the jaw support 5 is formed of bite blocks 10 and interceptors 11 which have cavities filled with a filling material 12 of predeterminable elasticity.

Figure 2:
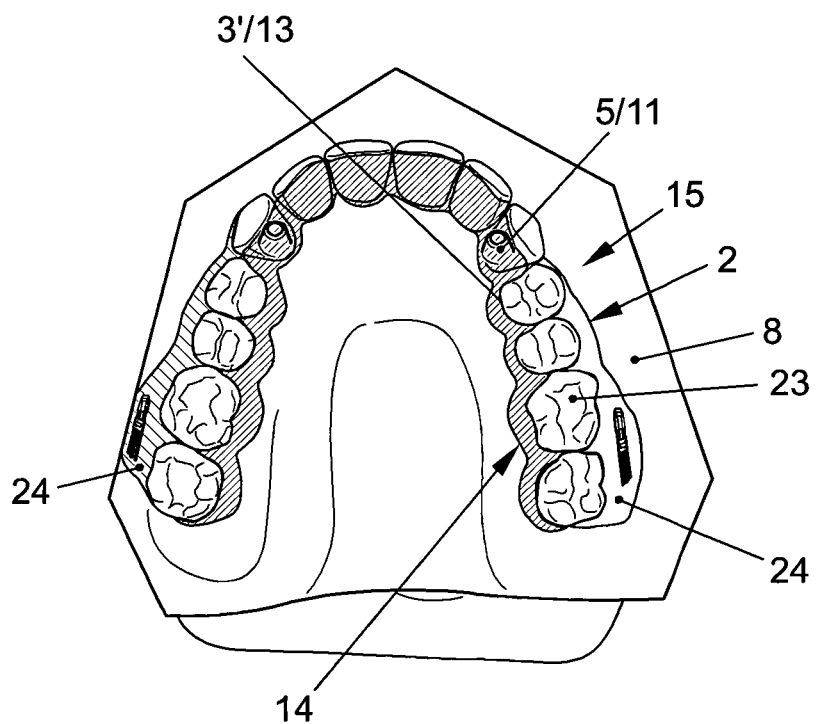
FIG. 2 is a bottom view of an apparatus in an embodiment of a maxillary apparatus.

The base module 2 has on its inner side a supplementary module 3 in the form of an expansion arch 13 affixed to the base module 2 (see FIG. 2).

In accordance with the exemplary embodiment of FIG. 8, the base module 2 has on its outer side 15 facing away from its inner side 14 receptacles 16 for auxiliary parts 17 which are bonded in place as attachments on the teeth (not shown) of a patient, and a grooved receiving part 18 for the connecting elements 9 that connect the module, such connecting elements being embodied as elastics 19.

The apparatus 1, also referred to here as an orthodontic 4-D apparatus, enables spatially controlled tooth movements and corrections of jaw position using the principles of spatial coupling and the sensorimotor control of masticatory forces as well as determinate elastic deformation.

Figure 20:
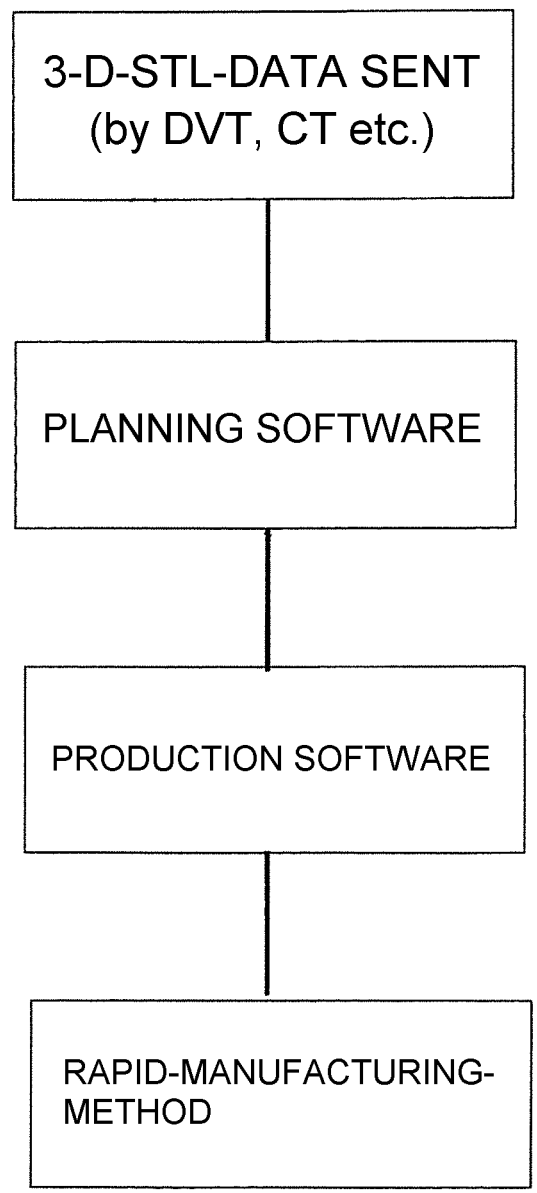
FIG. 20 is a flow chart illustrating a sequence of process steps for the manufacture of the apparatus.

In accordance with FIG. 20, a 3-D STL data set containing the three-dimensional geometry of the tooth rows and the temporomandibular joints, possibly also including bite registration, is determined by means of DVT, CT, etc.

In the next step, software (4-D planning software) is used to calculate and simulate how the teeth 22, 32 of both jaws 7, 8 must be moved in order to support both temporomandibular joints 33 in the desired position at least through tripodization (supporting of side teeth and one tooth in the anterior area, i.e. a three-point mounting between maxilla 8 and mandible 7).

In a following step, the necessary base modules 2 and their connection by means of their base clips 27 as well as the incremental deformation of all components are planned using 4-D production software.

For the actual production of the apparatuses 1 and their base modules 2, rapid manufacturing methods, in particular 3-D printing methods, suggest themselves in order to handle the necessary variable geometries and material combinations of the apparatuses and base modules in a single production cycle.

Figure 11:
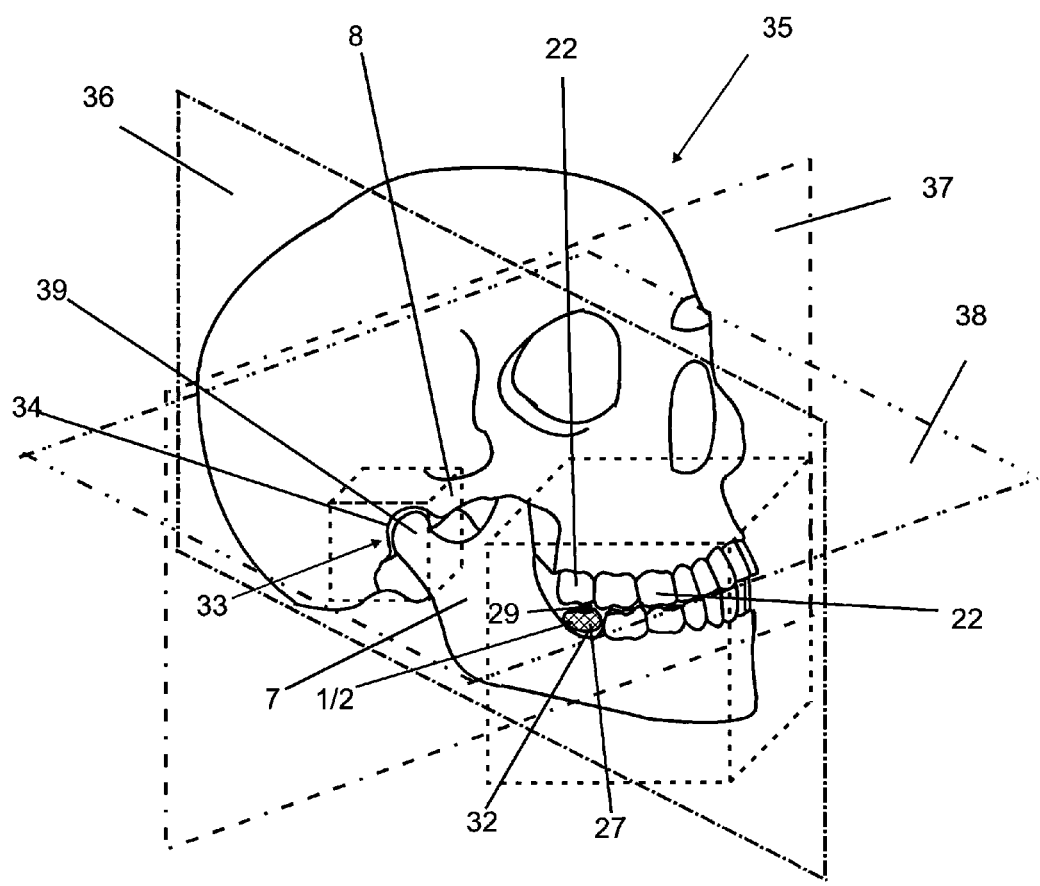
FIG. 11 is a perspective view of a skull with sectional planes indicated by dashed lines and representation of the three-dimensional tooth rows and of the temporomandibular joints as well as the principle of spatial coupling between tooth rows and the temporomandibular joints as a "fourth dimension" and the depiction of a base module.

FIG. 11 shows a skull 35 with a vertical plane 36 indicated by dashes, a transverse plane 37, and a horizontal plane 38. The teeth 21 of the maxilla 8 are connected with the Os temporale, the joint bearing 34 of the temporomandibular joints 33, by means of the principle of spatial coupling. The teeth 32 of the mandible 7 are spatially connected with the condylus, the joint head 39 of the temporomandibular joint 33, in pairs on the right and left sides, by means of the mandible 7.

Thus, whenever a bite is carried out, the spatial position of both temporomandibular joints 33 is determined by the positions of the tooth contacts. The vertical change of a single tooth 32 in particular automatically results in a calculable change to the temporomandibular joints on both sides.

In accordance with FIGS. 12 and 13, an apparatus 1 may consist of only a single base module 2. In that case the base module 2 has a base clip 27 with a functional hollow body 29 having a cavity 40 arranged in [???] the area of the tooth crown of a tooth 32 that needs to be covered. The predetermined resistance form of the filled functional hollow body 29 largely determines its deformability. A circumferential pressure transfer ring 30, with a gaseous or liquid filling of the cavity, serves as a seal against the occlusal surface 42 of the tooth crown 28 under the effects of masticatory pressure. The base clip 27 serves to reversibly secure the position of the functional hollow body 29 between the tooth crowns 28. Multiple functional elements may be connected with one another by extension of the base clip 27.

The elastic characteristics of the functional hollow body 29 (including its damping) depend largely on the compressibility of the filling, i.e. the filling material 12, under masticatory pressure. A polysaccharide layer 41 on the tooth crown 28 improves the seal of the cavity 40 in the event that a gaseous filling material 12 is used. The prosthetic equator 31 is overlapped by the base clip 27 of the base module for the purpose of establishing retention. The buccolingual extension of the occlusal functional hollow body support always lies within the extension of the prosthetic equator 31 for the purpose of creating a seal.

FIG. 13 depicts a base module 2, the functional hollow body 29 of which is suited as an element for auto-leveling. The resistance form of the functional hollow body 29 is calculated such that the resistance against the masticatory pressure increases with deformation. The neuromuscular system stops the vertical reduction of the functional hollow body 29 as soon as the sensorially correct dimension has been reached.

Figures 14, 15, 16:
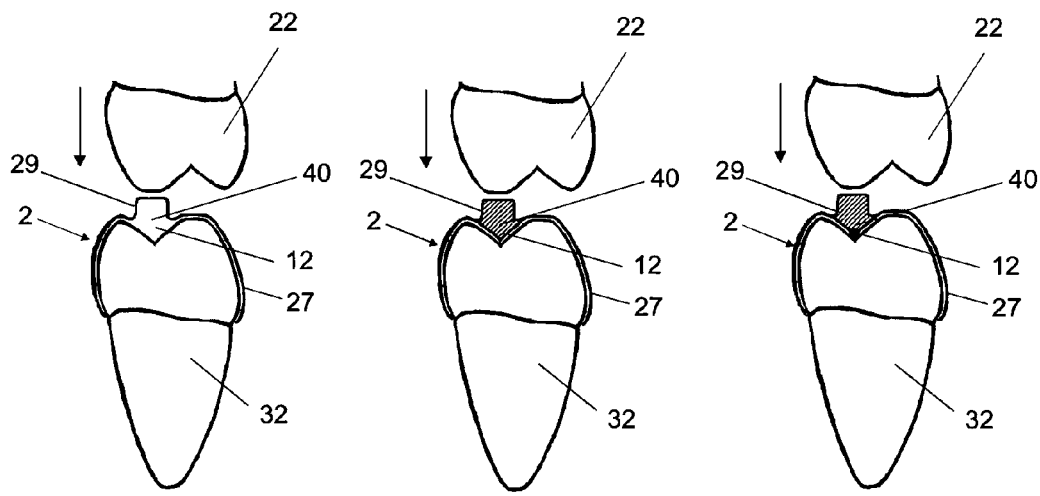
FIG. 14 is a lateral sectional view of a further base module installed on the associated tooth and a tooth outlined on the jaw opposite.
FIG. 15 is a lateral sectional view of a further base module installed on the associated tooth and a tooth outlined on the jaw opposite.
FIG. 16 is a lateral sectional view of a further base module installed on the associated tooth and a tooth outlined on the jaw opposite.

FIG. 14 accordingly depicts a cavity 40 filled with a gaseous filling material 12. The gas filling provides a strong resistance form. The resistance form permits only minor deformations. The planar surface of the functional hollow body 29 cushions the tip contact of the opposing tooth 22. The gas filling damps the cushioning effect. Thus, with continued application of pressure, a slight intrusion of both teeth results.

The base module 2 in accordance with FIG. 15 has a filling material 12 which is of elastic consistency.

By means of the counterbearing a vertical distance of adjacent teeth is always pretensioned so that essentially one or more neighboring teeth can also be moved vertically by means of a preconfigured deformation of the base clip 27 expanded to neighboring teeth.

FIG. 16 depicts a base module 2 of a functional hollow body 29 equipped with a filling which is very hard at least in the tip facing toward the tooth, and which vertically and directly sharply affects the dermodontal sensory apparatus when subjected to occlusion pressure. The masticatory pressure in this position is consequently reflexively released and shifted in favour of another tooth movement. The hard core of the filling material 12 thus triggers the "cherry pit reflex".

Figure 17:
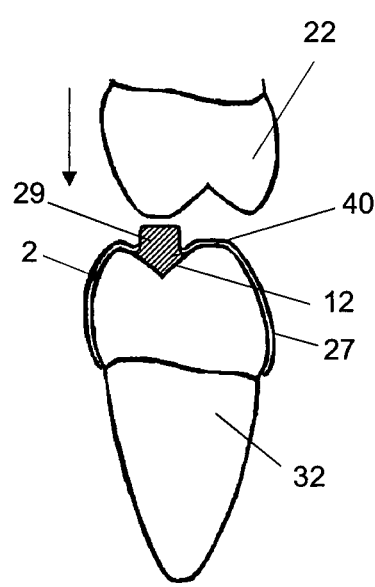
FIG. 17 is a lateral sectional view of a further base module installed on the associated tooth and a tooth outlined on the jaw opposite.

FIG. 17 depicts a base module 2 in which the cavity 40 of the functional hollow body 29 has a soft elastic filling. Due to the soft elastic filling, the base module 2 functions as an intrusion element.

Figure 18:
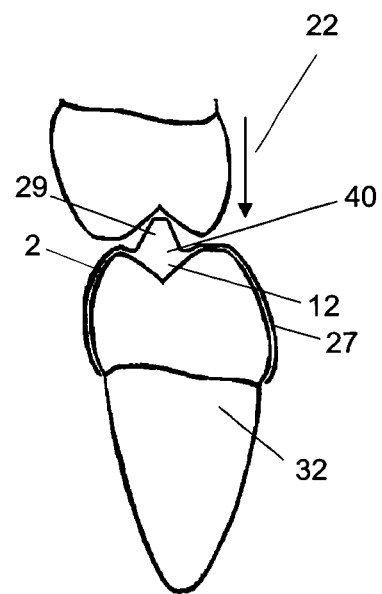
FIG. 18 is a lateral sectional view of a further base module installed on the associated tooth and a tooth outlined on the jaw opposite.

The base module 2 of FIG. 18 functions as an inter-cusp element. With its functional hollow body 29, this base module 2 has all the features of the base element 2, but can be positioned between the cusps of the opposing, tooth 22, by virtue of its incisally narrow shape.

FIG. 20 depicts a sequence of process steps for the manufacture of an apparatus 1 in which the form, i.e. the geometry of the base modules, is modified in each case in a series of precalculated stages.

Figure 19:
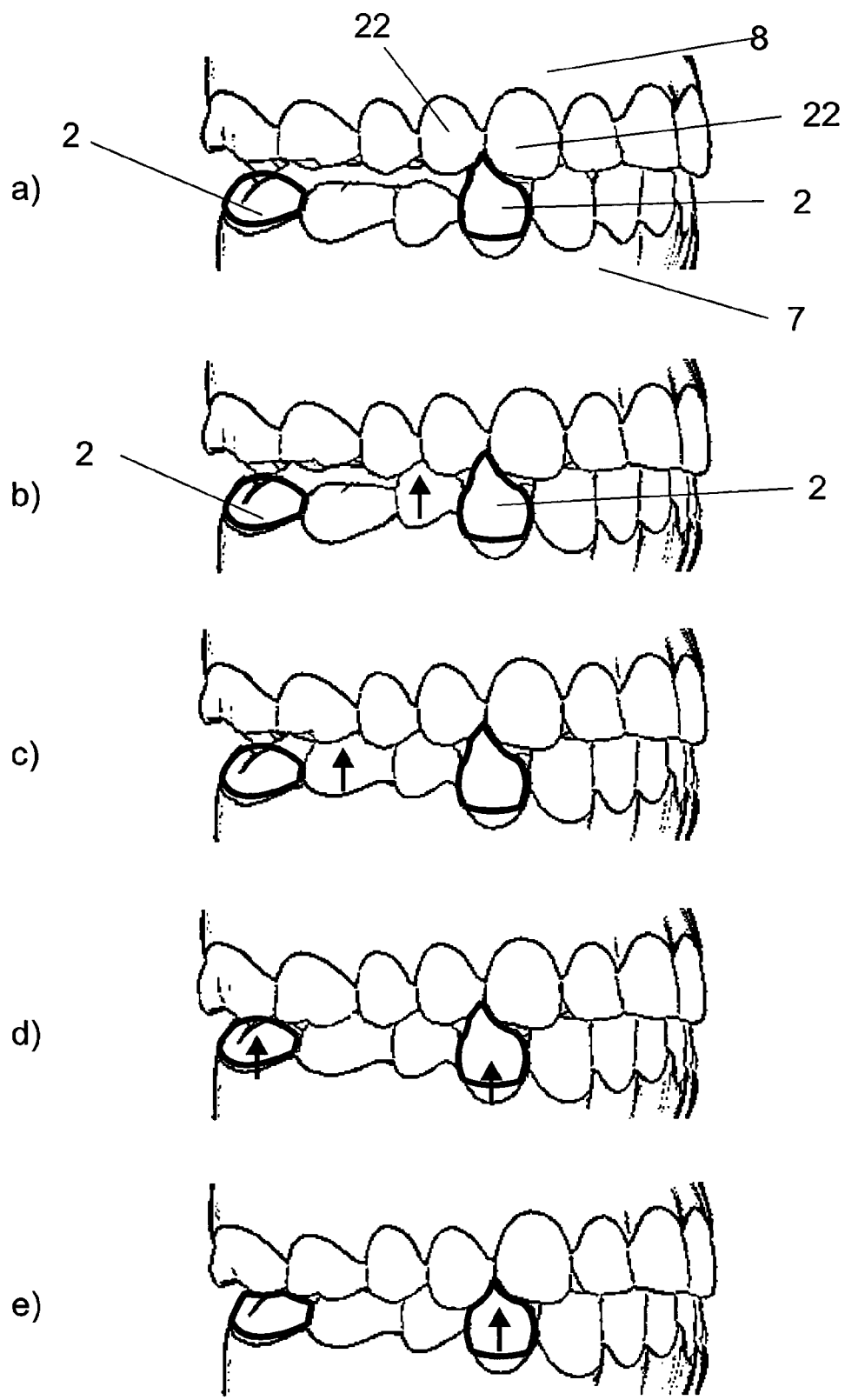
FIGS. 19a to 19e illustrate a sequence of lateral views of the occlusion-borne supports on the teeth with incrementally geometrically reduced functional hollow bodies of the base modules.

In accordance with FIGS. 19a and 19b, the form of the base modules 2 is changed the teeth 22 such that the teeth 32 of the mandible 7 can also be extruded in a controlled manner. By replacing the apparatus 1 formed by the base modules 2 with functional hollow bodies 29 reduced geometrically in increments, the teeth are also brought into occlusal contact with the functional hollow bodies 29.

In a first step for producing an apparatus 1, a spatially three-dimensionally defined positional relationship between maxilla 8 and mandible 7 is produced by modifying the form of the tooth surface using the wax-up technique in an articulator 20. In a second step, an overimpression of the model geometry as reconfigured with bite blocks 10 and interceptoren is created by physical or optical impression. In a third step, the jaw relation of a patient previously transferred to the articulator 20 is transferred to a known setup model 21 which is generated using an analog or digital process. The teeth 22 of the setup model 21 can be moved into the positions intended by the user/treating professional.

The apparatus 1 is adjusted in steps for the incremental movement of teeth, and corresponding different modules 2, 3 are produced.

FIG. 2 depicts in a top view an occlusion-bearing surface 23 of a base module 2. A supplementary module 24 for distalizing individual teeth is attached to the base module 2 via a screw element 25 (see FIGS. 1, 2, 3).

Figure 3:
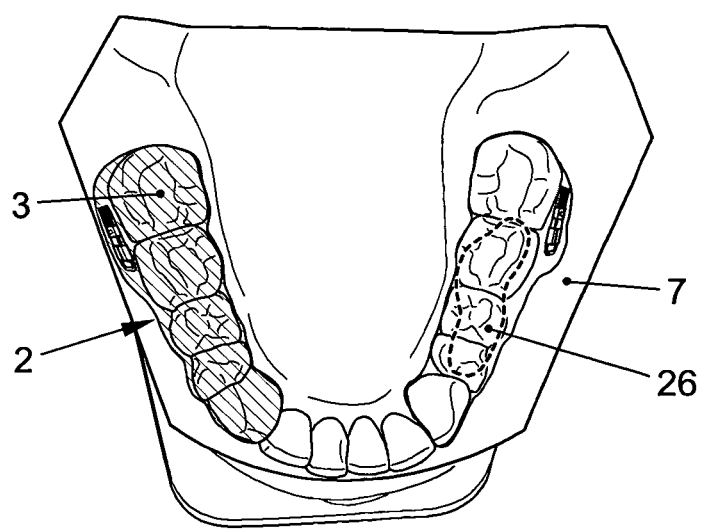
FIG. 3 is a top view of an apparatus in an embodiment of a mandibular apparatus.

FIG. 3 shows the embodiment of a mandibular apparatus in which the functional-therapeutically effective surface of the base module 2 is depicted with dashed lines.

Of course, the embodiments discussed in the specific description and shown in the Figures are merely illustrative exemplary embodiments of the present invention. In the light of the present disclosure a person skilled in the art has a broad spectrum of optional variations available.

LIST OF REFERENCE NUMBERS

1 Apparatus
2 Base modules
3, 3' Supplementary module
4 Auxiliary part
5 Jaw support
6 Functional module
7 Mandible
8 Maxilla
9 Connecting element
10 Bite block of 5
11 Interceptor of 5
12 Filling material of 10, 11
13 Expansion arch of 3
14 Inner side of 2
15 Outer side of 2
16 Receptacles of 2
17 Auxiliary means
18 Grooved receiving element of 17
19 Elastic of 9
20 Articulator
21 Setup model
22 Teeth of 21
23 Occlusion-bearing surface
24 Supplementary module
25 Screw elemen
26 Functional-therapeutic surface
27 Base clip of 5
28 Tooth crown of 32
29 Functional hollow body of 27
30 Pressure transfer ring of 29

31 Prosthetic equator of 28
32 Tooth
33 Temporomandibular joint
34 Joint bearing of 33
35 Skull
36 Vertical plane
37 Transverse plane
38 Horizontal plane
39 Joint head of 33
40 Cavity of 29
41 Polysaccharide layer
42 Occlusion surface

The invention claimed is:

1. An apparatus (1) for temporomandibular joint-related corrections of tooth position, taking into account a variant of the registration or construction of the bite predetermined by a user, comprising:
   a base module (2) extending at least on an occlusion-bearing part of one side of the jaw, the base module (2) being supported in an intermaxillary manner and having tooth-accommodating cavities to accommodate teeth, so that tension forces necessary for tooth movements can act on the teeth (22),
   the base module (2) having a three-dimensionally defined jaw support (5) designed in accordance with specifications of the user,
   the jaw support (5) being formed by bite blocks (10) and/or interceptors (11) that have filling-material cavities (40) in the area of the tooth crown (28) filled with a filling material (12) of predeterminable elasticity for vertical corrections of the alveolar processes in the form of intrusion or extrusion of the tooth (32),
   the base module (2) having a base clip (27) with a functional hollow body (29) facing an opposing jaw as part of the bite block (10) or the interceptor (11),
   the functional hollow body (29) being filled with the filling material (12), and
   the functional hollow body (29) having a circumferential pressure transfer ring (30) facing the occlusion surface of the covered tooth crown (28).

2. The apparatus according to claim 1, wherein the base clip (27) overlaps the prosthetic equator (31) of the tooth crown (28).

3. The apparatus according to claim 1, wherein auxiliary parts (4) are provided.

4. The apparatus according to claim 1, wherein the base module (2) has connected to it a functional module (6) that can be reused when the base module (2) is modified.

5. The apparatus according to claim 4, wherein the base module (2) can interact with a supplementary module (3) that can be arranged on the opposing jaw.

6. The apparatus according to claim 5, wherein the base module (2) or its functional module (6) is connected to the supplementary module (3) by an elastic connecting element (9).

7. The apparatus according to claim 1, wherein the base module (2) has on its inner side (14) a supplementary module (3, 23) in the form of an expansion arch (13) affixed to the base module (2).

8. The apparatus according to claim 1, wherein the base module (2) has receptacles for auxiliary parts (17) on its outer surface (15) facing away from the inner side (14).

9. The apparatus according to claim 1 wherein the receptacles (16) form receiving pockets for the auxiliary parts (17), which are embodied as attachments arranged on the outer side of teeth (22) and which have a grooved receiving element (18) for elastics (19) connecting the modules.

10. The apparatus according to claim 2, wherein auxiliary parts (4) are provided.

11. The apparatus according to claim 10, wherein the base module (2) has connected to it a functional module (6) that can be reused when the base component (2) is modified.

12. The apparatus according to claim 11, wherein the base module (2) can interact with a supplementary module (3) that can be arranged on the opposing jaw.

13. The apparatus according claim 12, wherein the base module (2) or its functional module (6) is connected to the supplementary module (3) by an elastic connecting element (9).

14. The apparatus according to claim 13, wherein the base module (2) has on its inner side (14) the supplementary module (3, 23) in the form of an expansion arch (13) affixed to the base module (2).

15. The apparatus according to claim 14, wherein the base module (2) has receptacles for auxiliary parts (17) on its outer surface (15) facing away from the inner side (14).

16. The apparatus according to claim 15, wherein the receptacles (16) form receiving pockets for the auxiliary parts (17) that define attachments arranged on the outer side of teeth (22) and that have a grooved receiving element (18) for elastics (19) connecting the modules.

17. The apparatus according to claim 2, wherein the base module (2) has connected to it a functional module (6) that can be reused when the base component (2) is modified.

18. The apparatus according to claim 17, wherein the base module (2) can interact with the supplementary module (3) that can be arranged on the opposing jaw.

19. The apparatus according to claim 18, wherein the base module (2) or its functional module (6) is connected to the supplementary module (3) by an elastic connecting element (9).

20. The apparatus according to claim 1, wherein the filling material is a gaseous or liquid material.

* * * * *